United States Patent
Frist, Jr.

(10) Patent No.: US 10,872,700 B1
(45) Date of Patent: Dec. 22, 2020

(54) SYSTEMS AND METHODS FOR AN ARTIFICIAL INTELLIGENCE SYSTEM

(71) Applicant: HealthStream, Inc., Nashville, TN (US)

(72) Inventor: Robert Frist, Jr., Nashville, TN (US)

(73) Assignee: HealthStream, Inc., Nashville, TN (US)

( * ) Notice: Subject to any disclaimer, the term of this patent is extended or adjusted under 35 U.S.C. 154(b) by 0 days.

(21) Appl. No.: 16/783,216

(22) Filed: Feb. 6, 2020

(51) Int. Cl.
| | |
|---|---|
| *G06F 40/205* | (2020.01) |
| *G16H 50/20* | (2018.01) |
| *G16H 70/40* | (2018.01) |
| *G16H 40/63* | (2018.01) |
| *H04W 4/14* | (2009.01) |
| *G16H 70/20* | (2018.01) |

(52) U.S. Cl.
CPC ........... *G16H 70/40* (2018.01); *G06F 40/205* (2020.01); *G16H 40/63* (2018.01); *G16H 50/20* (2018.01); *H04W 4/14* (2013.01); *G16H 70/20* (2018.01)

(58) Field of Classification Search
CPC ...................................... G16H 70/40
USPC ........................................ 705/2, 3
See application file for complete search history.

(56) References Cited

U.S. PATENT DOCUMENTS

| | | | |
|---|---|---|---|
| 4,895,518 A * | 1/1990 | Arnold ..................... | G09B 7/00 434/118 |
| 7,013,325 B1 | 3/2006 | Vivian et al. | |
| 7,731,500 B2 | 6/2010 | Feygin et al. | |
| 7,993,290 B2 | 8/2011 | Lund et al. | |
| 8,034,006 B2 | 10/2011 | Celik-Butler et al. | |
| 8,192,367 B2 | 6/2012 | Myklebust et al. | |
| 8,333,720 B2 | 12/2012 | Nysaither | |
| 8,394,040 B2 | 3/2013 | Strand et al. | |
| 8,465,292 B2 | 6/2013 | Nysaether et al. | |
| 8,594,996 B2 * | 11/2013 | Liang ..................... | G06F 40/10 704/9 |
| 8,827,708 B2 | 9/2014 | Christiansen et al. | |
| 8,939,922 B2 | 1/2015 | Strand et al. | |
| 9,886,873 B2 | 2/2018 | Patrickson et al. | |
| 10,438,487 B2 | 10/2019 | Patrickson et al. | |
| 10,438,497 B2 | 10/2019 | Patrickson et al. | |

(Continued)

OTHER PUBLICATIONS

Riccardo Miotto et al., "Deep learning for healthcare: review, opportunities and challenges." Briefings in Bioinformatics, 19(6), 2018, 1236-1246. (Year: 2018).*

(Continued)

*Primary Examiner* — Aryan E Weisenfeld
*Assistant Examiner* — Joshua B Blanchette
(74) *Attorney, Agent, or Firm* — Andre J. Bahou; Christopher T. McNeill; Waller Lansden Dortch & Davis LLP

(57) ABSTRACT

A method is disclosed, which may include generating, in a natural language processing (NLP) system, a plurality of entity data objects. The method may include generating, in the NLP system, a plurality of activity data objects. The method may include generating, on at least one server, an evaluation data object. The evaluation data object may include a problem data object, an observation data object, or an action data object. The method may include configuring each problem data object, observation data object, or action data object of the evaluation data object with a scoring rubric. Other methods, systems, and computer-readable media are also disclosed.

13 Claims, 14 Drawing Sheets

(56) References Cited

U.S. PATENT DOCUMENTS

| | | |
|---|---|---|
| 2002/0127525 A1 | 9/2002 | Arington et al. |
| 2003/0149759 A1 | 8/2003 | Hetherington et al. |
| 2003/0158467 A1* | 8/2003 | Liebert .................. G06Q 50/24 600/300 |
| 2005/0277096 A1 | 12/2005 | Hendrickson et al. |
| 2006/0069326 A1 | 3/2006 | Heath |
| 2007/0299473 A1 | 12/2007 | Matos |
| 2008/0171311 A1 | 7/2008 | Centen et al. |
| 2009/0035740 A1 | 2/2009 | Reed et al. |
| 2009/0148821 A1 | 6/2009 | Carkner et al. |
| 2010/0028846 A1* | 2/2010 | Cohen .................... G09B 7/00 434/323 |
| 2011/0117878 A1 | 5/2011 | Barash et al. |
| 2012/0301864 A1* | 11/2012 | Bagchi .................... A61B 5/00 434/362 |
| 2012/0310103 A1 | 12/2012 | Musiol et al. |
| 2013/0280685 A1 | 10/2013 | Patrickson et al. |
| 2014/0062694 A1 | 3/2014 | Miladin et al. |
| 2014/0272869 A1 | 9/2014 | Hambleton et al. |
| 2014/0277228 A1 | 9/2014 | Quan et al. |
| 2015/0154367 A1 | 6/2015 | Shetty et al. |
| 2015/0242498 A1 | 8/2015 | Davis |
| 2015/0363572 A1 | 12/2015 | Myklebust et al. |
| 2016/0148114 A1* | 5/2016 | Allen .................... G16H 10/60 706/11 |
| 2017/0061301 A1* | 3/2017 | Glass .................... G06N 5/046 |
| 2017/0084163 A1 | 3/2017 | Shen |
| 2017/0161439 A1 | 6/2017 | Raduchel et al. |
| 2018/0113867 A1* | 4/2018 | Erpenbach ............ G06F 16/243 |
| 2018/0144656 A1 | 5/2018 | Mitros |
| 2018/0293802 A1* | 10/2018 | Hendricks ............. G09B 23/30 |
| 2018/0342179 A1 | 11/2018 | Barash et al. |
| 2019/0139631 A1* | 5/2019 | Eshelman ............. G06N 20/00 |
| 2019/0340943 A1 | 11/2019 | Jimenez et al. |
| 2020/0105405 A1* | 4/2020 | Brandt ............ G06Q 10/06398 |

OTHER PUBLICATIONS

Benjamin Shickel et al. "Deep EHR: A Survey of Recent Advances in Deep Learning Techniques for Electronic Health Record (EHR) Analysis." IEEE J Biomed Health Inform. Sep. 2018 ; 22(5): 1589-1604. (Year: 2018).*

Zengjian Liu et al., "Entity recognition from clinical texts via recurrent neural network" BMC Medical Informatics and Decision Making 2017, 17(Suppl 2):67 (Year: 2017).*

Rouse, Margaret, "What is IBM Watson Assistant? Definition from WhatIs.com," Jul. 2018, WhatIs.com, whatis.techtarget.com/definition/IBM-Watson-Assistant.

"Watson Assistant—IBM Cloud," Feb. 3, 2020, IBM.com, https://web.archive.org/web/20200203010741/https://www.ibm.com/cloud/watson-assistant/.

* cited by examiner

SYSTEMS AND METHODS FOR AN ARTIFICIAL INTELLIGENCE SYSTEM

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to artificial intelligence. More particularly, the present disclosure relates to systems and methods for an artificial intelligence system.

Conventional approaches to computer-simulated medical training includes many downsides. For example, it can be difficult for a computer to evaluate a trainee's free-form response, which usually results in a human instructor evaluating the response. Furthermore, conventional computer-provided medical training simulations are not tailored to a trainee, but instead provide general-purpose simulations.

What is needed then are improvements to systems and methods for an artificial intelligence system.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure includes a method. The method includes generating, in a natural language processing (NLP) system, a plurality of entity data objects. Each entity data object includes a first entity key and one or more entity values corresponding to the first entity key. The method includes generating, in the NLP system, a plurality of activity data objects. Each activity data object includes a first activity key and one or more activity values corresponding to the first activity key. The method includes generating, on at least one server, an evaluation data object. The evaluation data object includes a problem data object. The problem data object includes at least one second entity key. The evaluation data object includes an observation data object. The observation data object includes at least one third entity key. The evaluation data object includes an action data object. The action data object includes at least one second activity key. The method includes configuring each problem data object, observation data object, and action data object of the evaluation data object with a scoring rubric.

Another aspect of the present disclosure includes a second method. The method includes presenting, via a user interface of a computing device, a user with medical scenario information. The method includes receiving, at least one server, a plurality of responses from the user. The plurality of responses include a problem response, an observation response, and an action response. The method includes sending the plurality of responses to a natural language processing (NLP) system. The method includes receiving, from the NLP system, at least one computer-readable parsing based on at least a portion of the plurality of responses. The method includes calculating, from the at least one computer-readable parsing, a score for the user. The score indicates a clinical judgement evaluation of the user.

Another aspect of the present disclosure includes a computer-readable storage medium. The computer-readable storage medium includes at least one processor. The computer-readable storage medium includes at least one memory storing one or more instructions. The at least one processor, in response to executing the one or more instructions, implements a method. The method includes sending, to a computing device, medical scenario information. The method includes receiving a plurality of responses from the user. The plurality of responses include a problem response, an observation response, and an action response. The method includes sending the plurality of responses to a natural language processing (NLP) system. The method includes receiving, from the NLP system, at least one computer-readable parsing based on at least a portion of the plurality of responses. The method includes calculating, from the at least one computer-readable parsing, a score for the user. The score indicates a clinical judgement evaluation of the user.

The systems and method of the present disclosure improve computer-provided medical training and computerized medical simulations. For example, by configuring an NLP system with a plurality of entity data objects, activity data objects, problem identity objects, observation data objects, and action data objects, many of which include corresponding keys and values, a trainee's response can be better evaluated by the NLP system to determine accuracy and completeness of the trainee's response. Furthermore, by obtaining data about the trainee, the simulation system tailors the simulations to focus on the needs and characteristics of the trainee.

The systems and methods of the present disclosure include improvements to computer functionality. For example, the systems and methods disclosed herein result in automated evaluation of responses from healthcare workers in training. The systems and methods described herein allow computing device to produce accurate and realistic medical training scenario conversations. Furthermore, the systems and methods of the disclosure allow a user in medical training to obtain almost instant feedback regarding a medical training scenario, instead of having to wait for a human to evaluate his or her performance, which happens in conventional approaches.

The systems and method of the present disclosure include unconventional elements and arrangement of elements. These elements and arrangements are not well-understood, routine, or conventional. For example, using a NLP system generate entity data objects and activity data objects that can be used to carry out a medical training conversation and evaluate a user's responses is not a well-understood, routine, or conventional activity. Prompting a user, via a text chat user interface, to identify a problem, observations, actions, and rationales so that they can be submitted in a free response format to a computer for automated grading is also unconventional, and not routine or well-understood.

Numerous other objects, advantages and features of the present disclosure will be readily apparent to those of skill in the art upon a review of the following drawings and description of a preferred embodiment.

DETAILED DESCRIPTION

Figure 1:
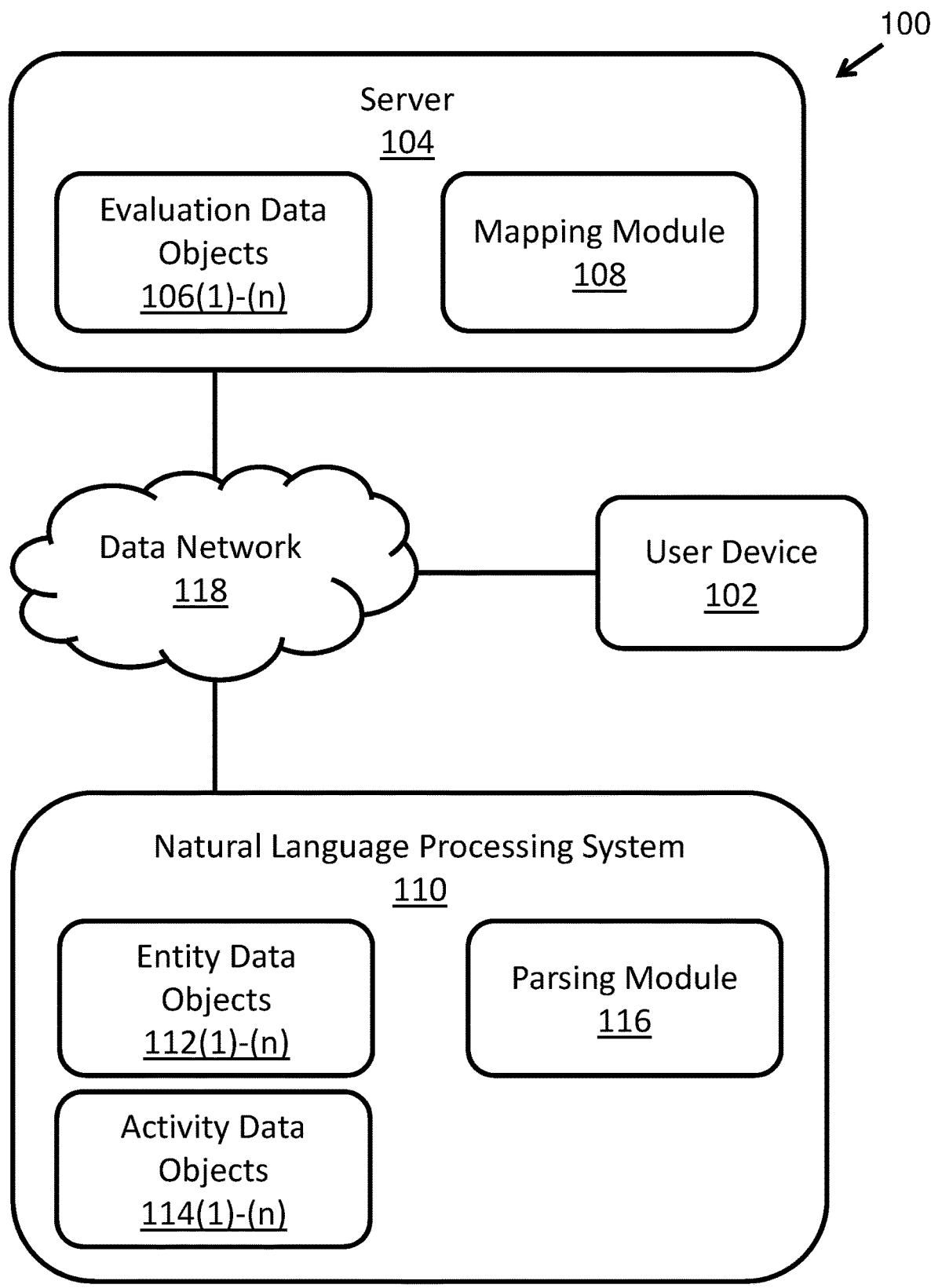
FIG. 1 is a schematic block diagram depicting one embodiment of a system for an artificial intelligence system.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

The terms "first," "second," "third," etc. may be used herein to describe various elements, although these elements should not be limited by these terms. These terms are used only to distinguish one element from another element. Thus, a first element could be termed a second element without departing from the teachings of the present disclosure. Furthermore, in some cases, a reference to a first element and a second element may refer to the same element or may refer to different elements. Also, a first element and a second element may each include a value, which may include the same value or different values. Lastly, the terms "first," "second," "third," etc. do not imply a specific ordering of elements unless explicitly stated.

As a general overview, one embodiment of the present disclosure is directed to systems and methods for an artificial intelligence (AI) system. The systems and methods of the disclosure provide medical training scenarios to users via a user interface of a user device. A user submits information via the user interface. The user may submit the information in the form of open responses (i.e., the user may submit free-form text or audio responses instead of selecting predetermined answers). The AI system parses the user-submitted information and determines a score for the user based on the presence or absence of data in the parsed user-submitted information. The score may reflect an evaluation of the clinical judgement of the user. Leveraging AI in the context of medical training, for example, allows for a more accurate and fair evaluation of a user's clinical judgement, and allows users to experience interactive training outside of in-person training events.

FIG. 1 depicts an exemplary embodiment of an artificial intelligence system 100 incorporating certain aspects of the disclosed embodiments. The system 100 includes a user device 102. The user device 102 may include a user interface. The user interface may display medical scenario information. A user of the user device 102 may enter responses prompted by the medical scenario information into the user interface.

In some embodiments, the system 100 includes a server 104. The server 104 may include a computing device. The server 104 may include a plurality of evaluation data objects 106(1)-(n). An evaluation data object 106 may include data that may be compared to a parsed version of the user's responses to determine a clinical judgement evaluation for the user. The server 104 may include a mapping module 108. The mapping module 108 may include software, hardware, or a combination of software and hardware. The mapping module 108 may map a computer-readable parsing of the user's responses to the data of one or more evaluation data objects 106(1)-(n).

In one embodiment, the system 100 includes a natural language processing (NLP) system 110. The NLP system 110 may include one or more computing devices. The NLP system 110 may parse responses from the user device 102. The NLP system 110 may include one or more entity data objects 112(1)-(n). A entity data object 112 may include data describing an entity. The NLP system 110 may include one or more activity data objects 114(1)-(n). An activity data object 114 may include data describing an activity or some other action. The NLP system 110 may include a parsing module 116. The parsing module 116 may parse user responses into computer-readable data that can used by one or more components of the system 100 such as the mapping module 108.

In some embodiments, the system 100 includes a data network 118. One or more components of the system 100 may be in data communication via the data network 118. In one embodiment, the data network 118 may include one or more devices that facilitate the flow of data from one device to another. The data network 118 may include routers, switches, transmission servers, or other networking devices. Portions of the data network 118 may include wired or wireless data transmission. The data network 118 may include one or more local area networks (LANs), wide area networks (WANs), the Internet, or some other network.

The following describes details of one or more embodiments of the present disclosure. In one embodiment, the user device 102 may include an electronic device. The user device 102 may include a computing device. A computing device may include a desktop computer, laptop computer, tablet computer, smartphone, smartwatch, application server, database server, or some other type of computing device. A computing device may include a virtual machine. The user device 102 may include a screen to display the user interface.

In some embodiments, the user interface may display one or more options for the user of the user device 102 to select. An option may correspond to a medical training scenario. The user interface may display limited information to the user before the user selects an option. For example, the user interface may display a general category of a possible medical training scenario (e.g., first aid, acute care, etc.), but may not display a specific medical problem or issue in that category (e.g., cardiac arrest, choking, etc.). Other information may be displayed on the option selection portion of the user interface. In response to the user selecting an option on the user interface, the server 104 may send corresponding medical scenario information to the user device 102.

Figure 2:
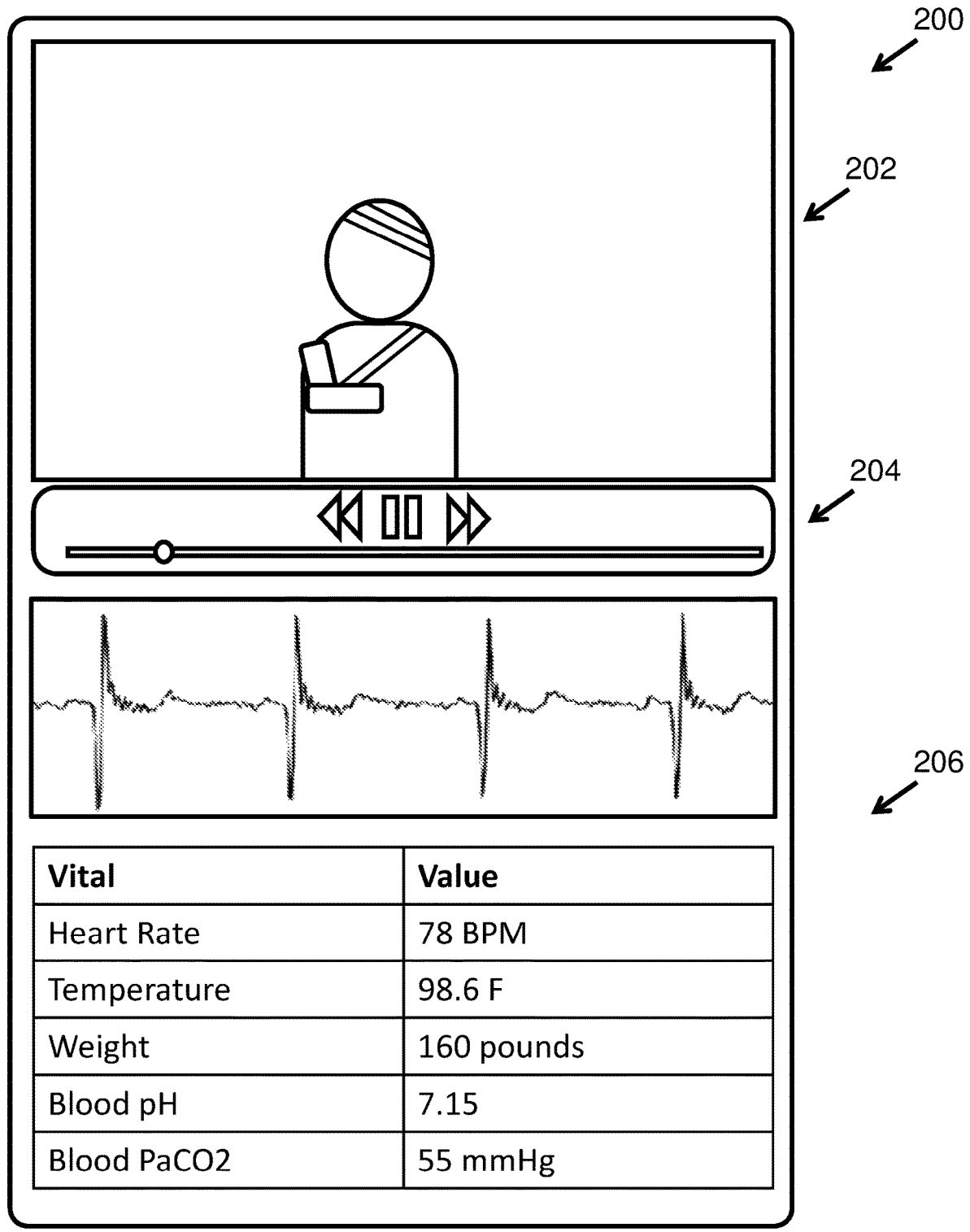
FIG. 2 is a front view depicting one embodiment of a user interface for a user device of an artificial intelligence system.

FIG. 2 depicts one embodiment of a user interface 200 displaying medical scenario information. Medical scenario information may include medical information corresponding to a training scenario that can be presented in a variety of formats. The medical scenario information may include a video 202. The video 202 may include an audio-visual presentation. The video 202 may include a video of a patient experiencing a medical episode. A user of the user device 102 may control playback the video 202 using a video control interface 204 of the user interface 200. The video control interface 204 may include buttons, sliders, or other widgets to adjust playback of the video. The video control interface 204 may allow the user to pause, play, fast-forward, or rewind the video 202, control the volume of the video 202, or otherwise interact with the video 202.

In one embodiment, the user interface 200 may include one or more vital signs 206. The one or more vital signs 206 may include an electrocardiogram (ECG) strip (e.g., a heart-beat monitor output), one or more lab values, or other medical information related to the medical training scenario. The one or more vital signs 206 may include a heart rate, temperature, weight, blood pH, blood PaCO2, or other vital signs of a patient. In some embodiments, the user of the user device 102 may use the medical scenario information to make decisions about the medical training scenario.

In some embodiments, the user device 102 may receive data including at least a portion the medical scenario information from the server 104. The server 104 may store the medical scenario information, for example, in a database or a file system on in or data communication with the server 104.

Figure 3A:
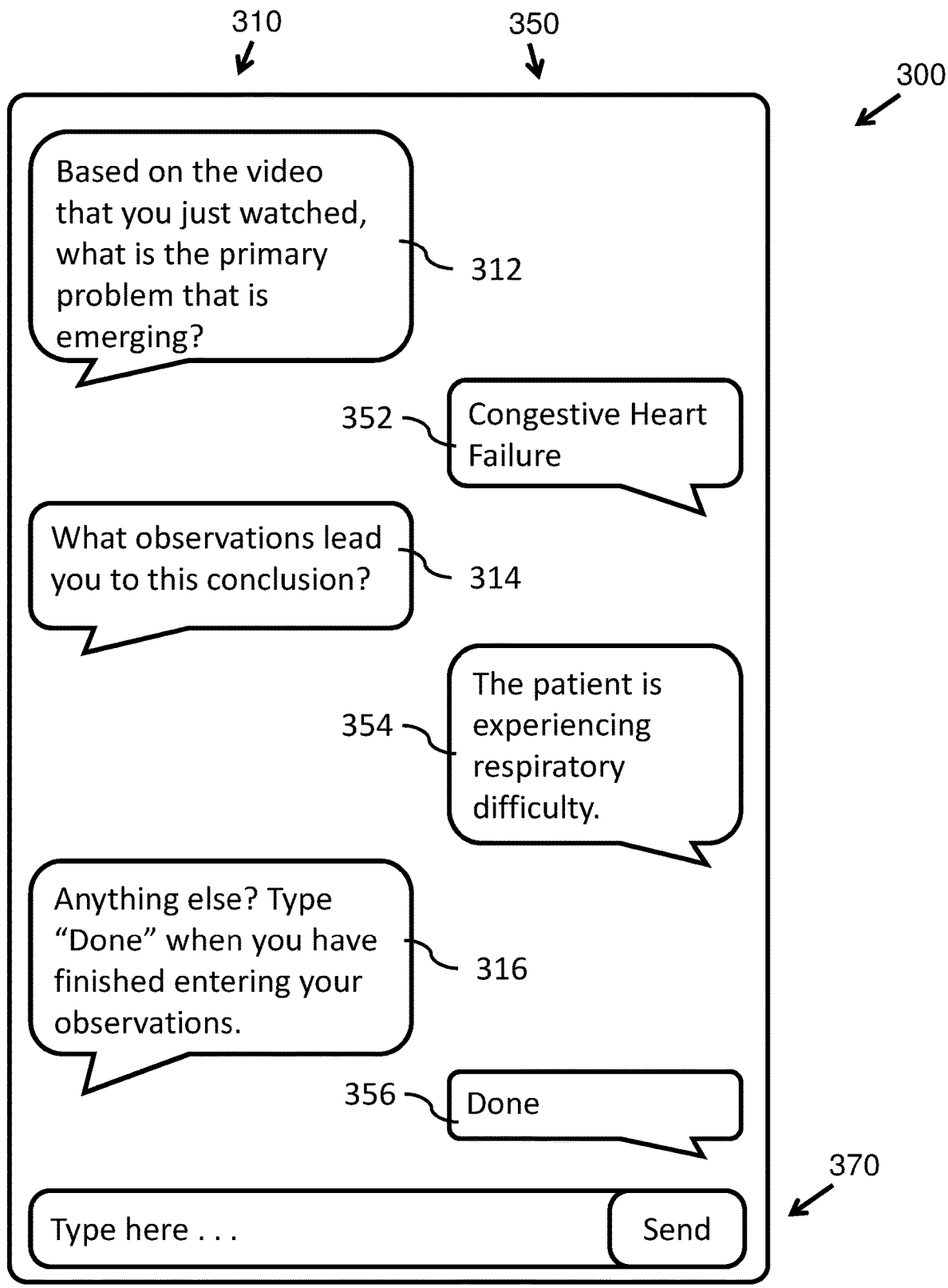
FIG. 3A is a front view depicting another embodiment of a user interface for a user device of an artificial intelligence system.
Figure 3B:
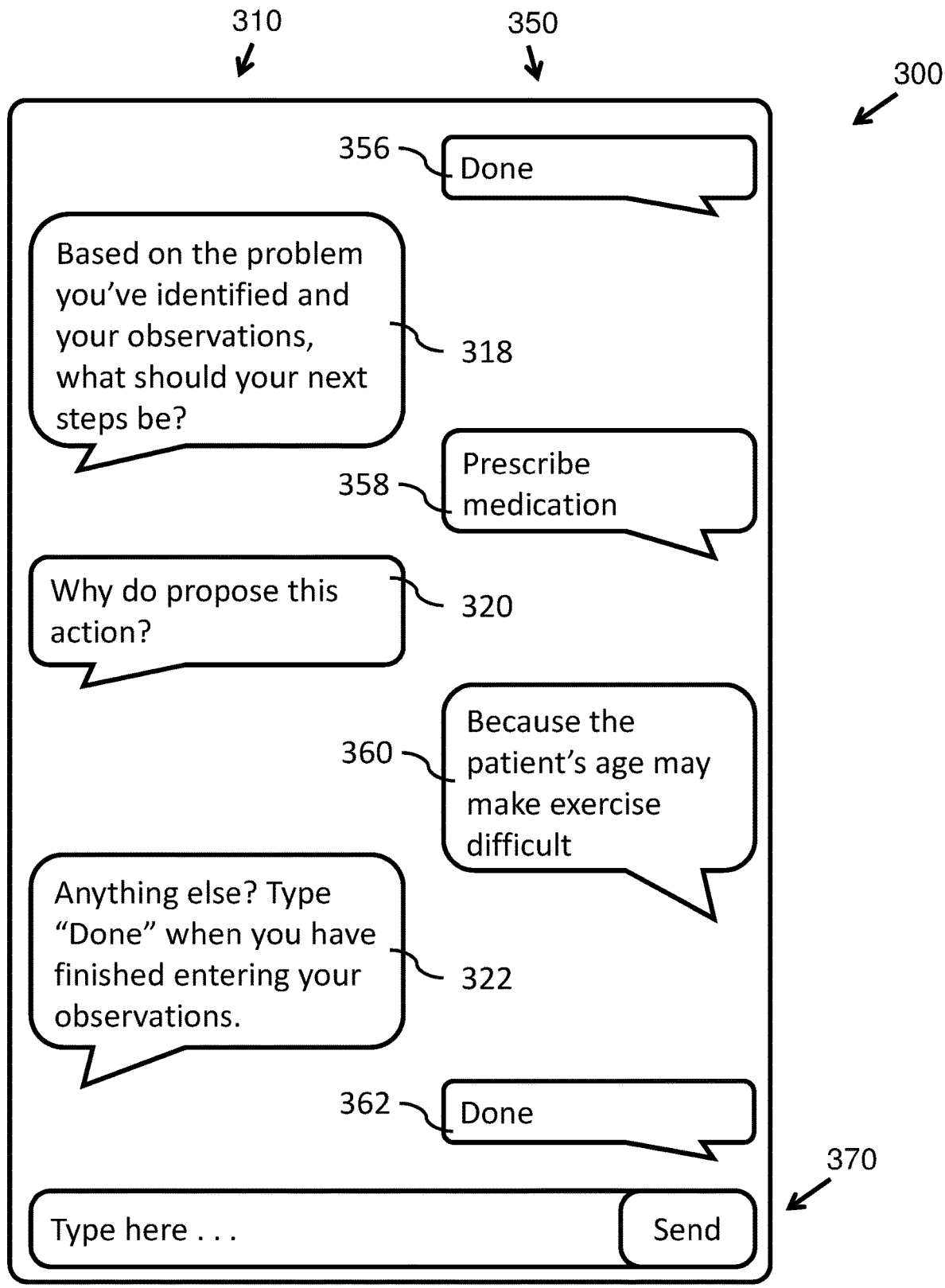
FIG. 3B is a front view depicting another embodiment of a user interface for a user device of an artificial intelligence system.

FIG. 3A and FIG. 3B depict exemplary embodiments of a user interface 300. The user interface 300 may include a text-chat interface. The text-chat interface may include one or more messages showing a conversation between multiple parties. The text-chat user interface may include an interface similar to a text message interface used in communicating via short message service (SMS) messages.

In one embodiment, the user interface 300 may include one or more server messages 310. A server message of the one or more server messages 310 may include a message sent from the server 104. The user interface 300 may include one or more user messages 350. A user message of the user messages 350 may include a message generated by the user of the user device 102. In one embodiment, a message of the server messages 310 or the user messages 350 may include text, images, video, audio, or data in another format.

In some embodiments, the server messages 310 may appear on one side of the user interface 300, and the user messages 350 may appear on the other side of the user interface 300. The user may enter his or her messages 350 as a string of text via a text entry area 370. Additionally or alternatively, the user may speak into the microphone of the user device 102, and the user device 102, the server 104, or the NLP system 110 may process the user's audio to generate the user's messages 350. In some embodiments, the user may attach one or more files to a user message 350 (such as an image, an audio file, a video file, or some other type of file). The user may use one or more buttons, scroll wheels, swipe motions, or other gestures to switch the user interface 300 between the text-chat user interface 300 of FIGS. 3A and 3B and the medical scenario information user interface 200 of FIG. 2.

As shown in FIG. 3A, in one embodiment, the user interface 300 may present one or more server messages 310 that include prompting questions or statements to the user of the user device 102. The user of the user device 102 may generate the user messages 350 to answer the one or more prompts about the medical scenario information depicted in FIG. 2.

In some embodiments, the user interface 300 may present the one or more server messages 310 in phases. For example, a first phase may include a problem phase. During the problem phase, one or more server messages 310 may prompt the user to respond with an identification of a problem that is emerging in the medical training scenario. A second phase may include an observation phase. During the observation phase, one or more server messages 310 may prompt the user to respond with one or more observations that the user may have observed in the medical training scenario. A third phase may include an action phase. During the action phase, one or more server messages 310 may prompt the user to respond with one or more actions that the user proposes taking in the medical training scenario. A fourth phase may include a rationale phase. During the rationale phase, one or more server messages 310 may prompt the user to respond with one or more rationales for taking a proposed action. The user interface 300 may allow the user to switch between phases. The user interface 300 may present the one or more phases in a variety of orders.

FIG. 3A and FIG. 3B depict an example of a text conversation between the user of the user device 102 and the server 104. A first server message 312 may include a message asking the user to identify one or more problems in the medical training scenario. A first user message 352 may include a problem response from the user. The problem response may include text data that includes a user's attempt to identify one or more problems. The problem response may include a diagnosis of a medical condition. The user may arrive at the diagnosis based on the medical scenario information.

A second server message 314 may ask the user what observation or observations led the user to his or her identification of the one or more problems. A second user message 354 may include an observation response. The observation response may include data that includes the user's observation or observations based on the medical scenario information. A third server message 316 may prompt the user to enter any additional observations that he or she may not have included in the second user message 354. In a third user message 356, the user may enter additional observations as an observation response, or the user may indicate that the user has no more observations to respond with.

FIG. 3B depicts one embodiment of a continuation of the conversation started in FIG. 3A. A fourth server message 318 may prompt the user to suggest one or more next steps to take in the medical training scenario. In a fourth user message 358, the user may include an action response. The action response may include data that includes one or more actions that the user may take if the medical training scenario presented in the medical scenario information were an actual medical scenario. The action response may be based on or may respond to the diagnosis identified in the problem response. In a fifth server message 320, the server 104 may ask why the user suggested the one or more next steps he or she suggested. The user, in a fifth user message 360, may include a rationale response. The rational response may include data including one or more rationales or explanations as to the suggested course of action contained in the previous message 358. A sixth server message 322 may ask if the user has any other information to add. The additional information may include additional problems, observations, actions, rationales, or other information. The user may use a sixth user message 362 to include the additional information or to indicate that the user wishes to enter no more information.

In one embodiment, the user device 102 may receive one or more server messages 310 over the data network 118 after the user device 102 sends each user message 350 over the data network 118. In another embodiment, the user device 102 may receive all server messages 310 corresponding to the medical training scenario before the text conversation occurs. Logic functionality (e.g., software) installed on the user device 102 may determine which server message 310 to display at specified times during the conversation. In some embodiments, the user device 102 may send at least a portion of the user messages 350 to the server 104. The user device 102 may send the user messages 350 to the server after each message has been entered by the user, at the end of the text-chat conversation, or at another time. The user device 102 may send other information to the server 104 at or around the same time as sending the one or more user messages 350. In some embodiments, the server 104 may send the user messages 350 to the NLP system 110 for processing. The NLP system 110 may process the user messages 350 by parsing them based on the entity data objects 112(1)-(n) and the activity data objects 114(1)-(n) of the NLP system 110.

As discussed herein, the term "data object" may refer to a logical container for data. A data object may include one or more pieces of data stored within the data object or referenced by the data object. These pieces of data may include variables, other data objects, values, fields, etc. A data object may include an instantiated class of a programming language or an object in an object-oriented programming framework. A data object may include a variable or a data structure. A data object may include a portion of a database, such as a record or a row. Other ways to logically store data may also be used. Different data objects may include data objects derived from different classes, templates, etc.

In one embodiment, the NLP system 110 may include one or more computing devices. The NLP system 110 may include a cloud computing platform, a supercomputer, compute cluster, or some other computing platform. The NLP system 110 may include AI or machine learning software to perform its natural language processing functionality. Examples of an NLP system 110 may include the WATSON system provided by IBM, the SIRI assistant provided by Apple, Inc., or the WOLFRAM ALPHA system provided by Wolfram Alpha, LLC.

Figure 4:
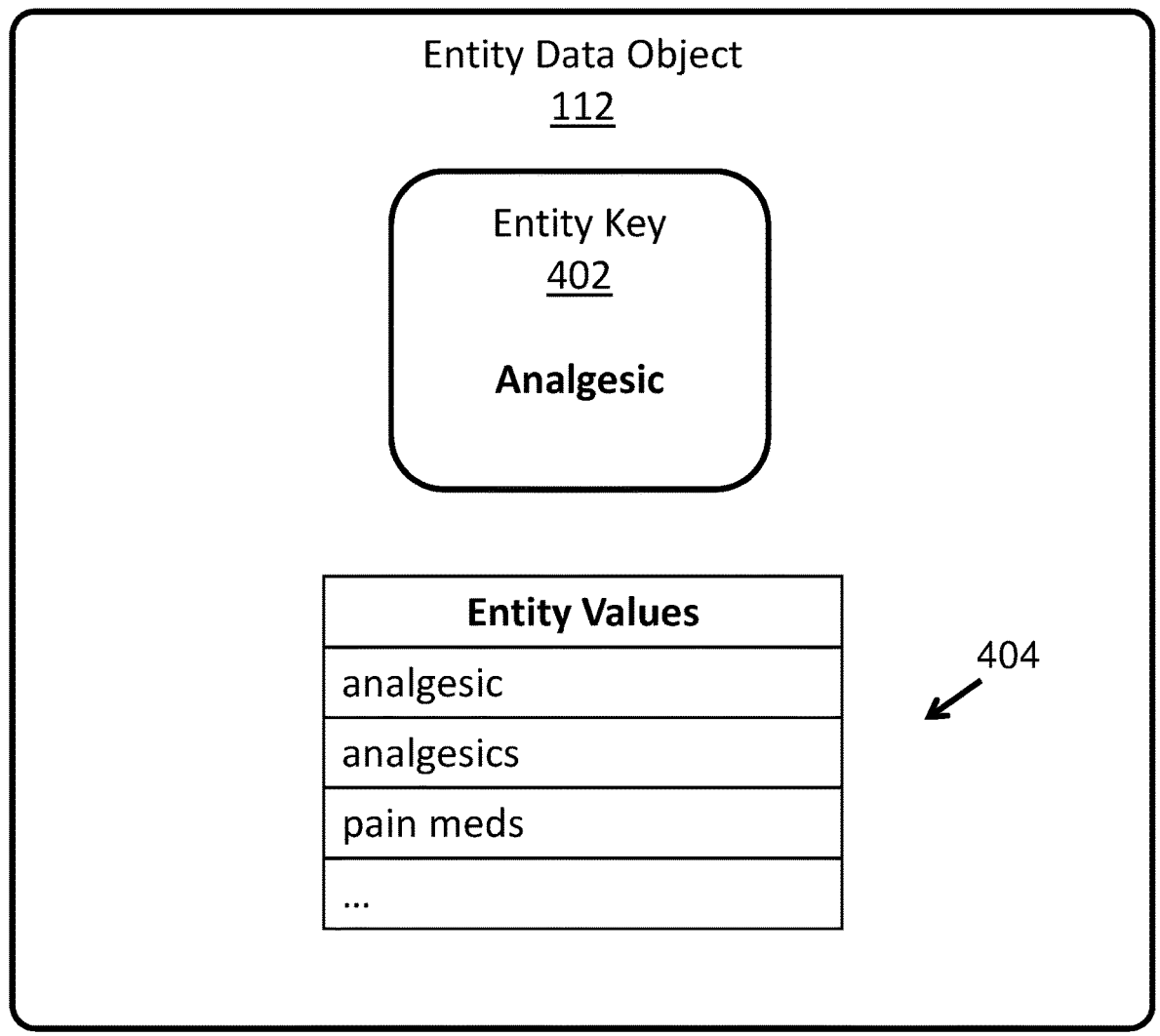
FIG. 4 is a schematic block view depicting one embodiment of an entity data object of an artificial intelligence system.

FIG. 4 depicts one embodiment of an entity data object 112. An entity data object 112 may include a data object that describes an entity. An entity may include an object, an idea, a person, a location, a noun, or the like. In one embodiment, an entity data object 112 may include an entity key 402. The entity key 402 may include a text string. The entity key 402 may uniquely identify the corresponding entity data object 112 among multiple entity data objects 112(1)-(n) of the NLP system 110.

In some embodiments, the entity data object 112 may include one or more entity values 404. The entity values 404 may correspond to the entity key 402. An entity value 404 may include a synonym of the entity key 402. The entity value 404 may include a type of the entity key 402. For example, as depicted in FIG. 4, the entity key 402 may include "Analgesic." The corresponding entity values 404 may include "analgesic," "analgesics," "pain meds," or other values.

In one embodiment, an entity key 402 may include a medical condition (e.g., congestive heart failure, bradycardia, etc.). An entity key 402 may include a medication (e.g., analgesic, opioid, etc.). An entity key 402 may include a medical device (e.g., an intravenous (IV) pole, an ECG monitor, etc.). An entity key 402 may include a medical supply (e.g., bandages, blood, etc.). An entity key may include a portion of human anatomy (e.g., blood, bones, heart, etc.).

Figure 5:
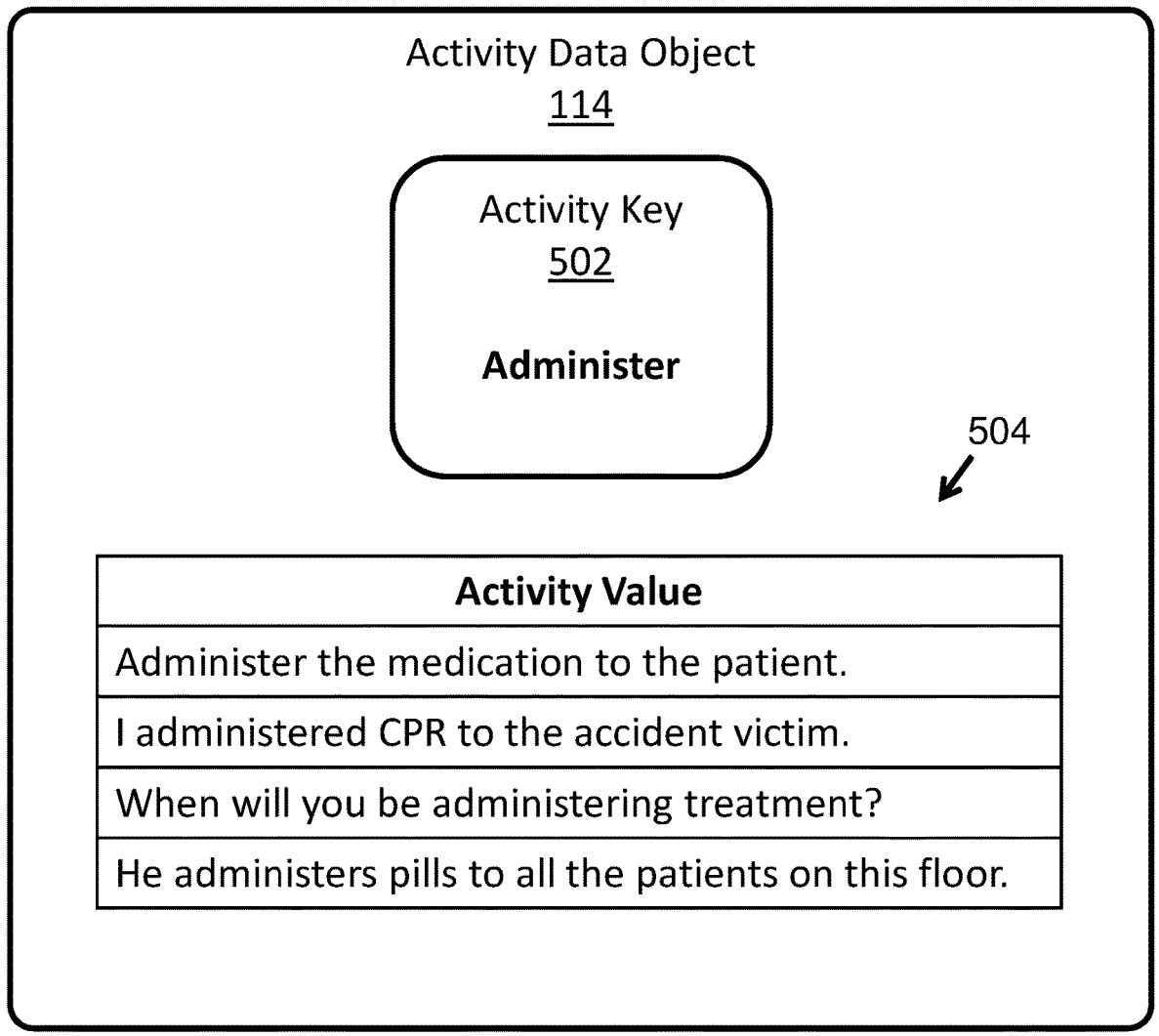
FIG. 5 is a schematic block view depicting one embodiment of an activity data object of an artificial intelligence system.

FIG. 5 depicts one embodiment of an activity data object 114. An activity data object 114 may include a data object that describes an activity. An activity may include an action, an act, a verb, or the like. In one embodiment, the activity data object may include an activity key 502. The activity key 502 may include a text string. The activity key 502 may uniquely identify the corresponding activity data object 114 from among multiple activity data objects 114(1)-(n) of the NLP system 110.

In one or more embodiments, the activity data object 114 may include one or more activity values 504. The activity values 504 may correspond to the activity key 502. An activity value 504 may include a synonym of the activity key 502. An activity value 504 may include a type of the activity key 502. In one embodiment, an activity value 504 may include a sentence that includes a use of the text of the activity key 502. A sentence may use the activity key in various ways, for example, as an infinitive, a conjugated verb, a past participle, an adverb, a gerund, or other forms. For example, as depicted in FIG. 5, the activity key 502 may include "Administer," and the corresponding activity values 504 may include sentences using the word "administer" in different forms and contexts.

In some embodiments, one or more entity data objects 112(1)-(*n*) or one or more activity data objects 114(1)-(*n*) may be grouped into a group. A single data object 112 or 114 may belong to multiple groups. In one embodiment, a group may include multiple data objects 112 or 114 that share a common characteristic. For example, a "Medication" group may include the entity data objects 112(1)-(*n*) that include entity keys 402 "Analgesic," "Antibiotic," "Laxative," "Opioid," or other entity keys 402.

In one embodiment, a user of the server 104 or the NLP system 110 may configure the entity data objects 112(1)-(*n*), activity data objects 114(1)-(*n*), groups of data objects 112, 114, or other data. For example, the entity data objects 112(1)-(*n*) may include separate entity data objects 112(1)-(*n*) for the entities "Physician," "Nurse," "Physician's Assistant," "Therapist," or other medical workers. In another example, the entity data objects 112(1)-(*n*) may include one entity data object 112 for "Healthcare Worker" and that entity data object 112 may include entity values 404 of "physician," "nurse," "physician's assistant," etc. Entity data objects 112(1)-(*n*), activity data objects 114(1)-(*n*), and groups of data objects 112, 114 may be configured in various ways.

In one embodiment, the parsing module 116 of the NLP system 110 may use the one or more entity data objects 112(1)-(*n*) and the one or more activity data objects 114(1)-(*n*) to parse one or more user messages 310. In one embodiment, the parsing module 116 parsing a user message of the one or more user messages 310 may include the parsing module 116 determining whether the user message includes text data that matches or corresponds to certain entity values 404 or activity values 504. In response to a user message including such text data, the parsing module 116 may generate a computer-readable parsing that includes one or more corresponding entity keys 402 or activity keys 502.

Figure 6:
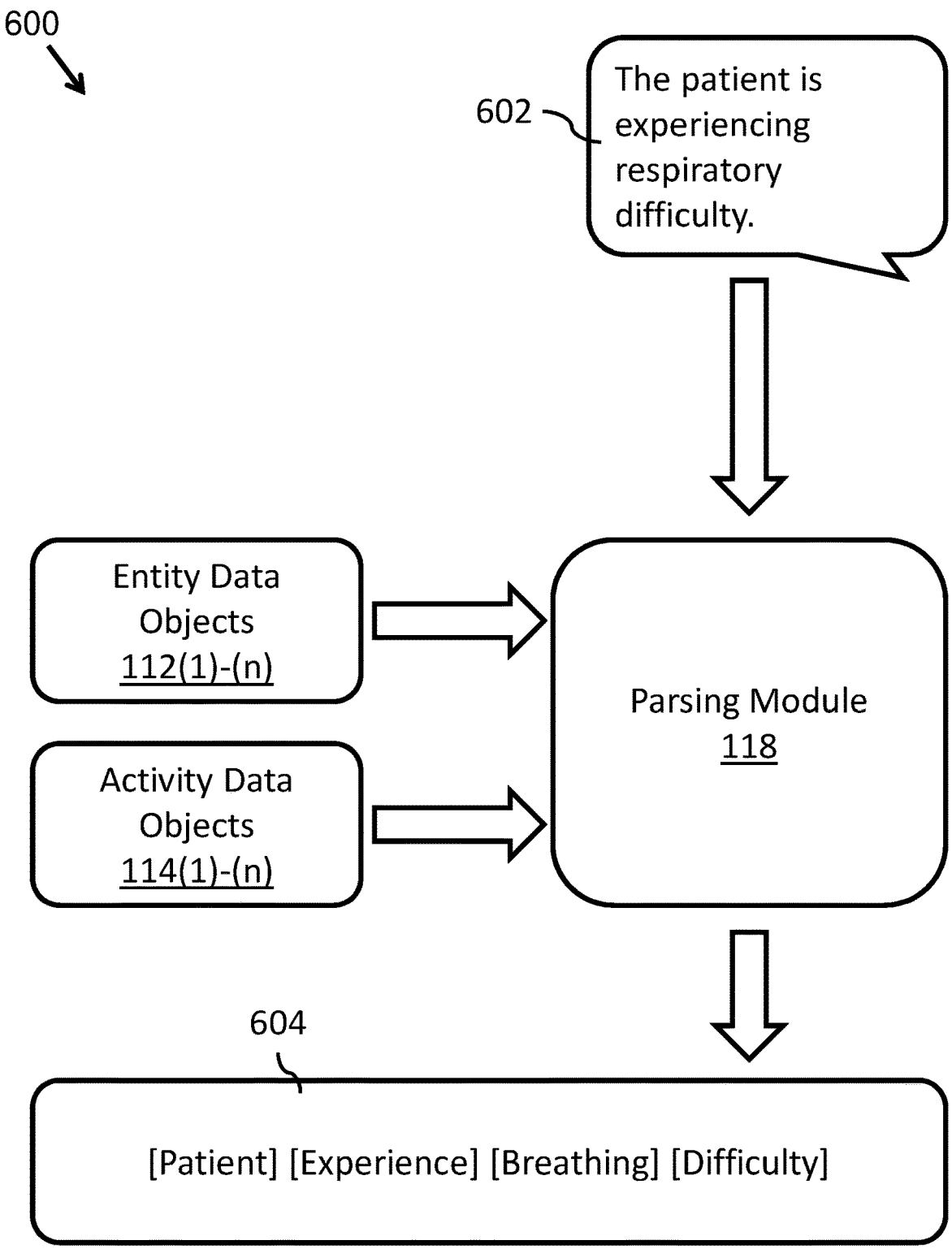
FIG. 6 is a schematic block view depicting one embodiment of a system for an artificial intelligence system.

FIG. 6 depicts one embodiment of a system 600. The system 600 may include a flow of data into the parsing module 116 of the NLP system 110 and a flow of data out of the parsing module 116. The flow of data depicted in FIG. 6 may occur within the NLP system 600.

In one embodiment, the parsing module 116 may receive, as input, a user response 602 from the user device 102. The user response 602 may include a user message of the user messages 350. For example, as depicted in FIG. 6, the user response 602 includes the user message 354 of the FIG. 3A. In some embodiments, the user response 602 may include metadata. The metadata may include data indicating the phase of the conversation that the user response 602 belongs to (e.g., the problem phase, the observation phase, the action phase, etc.). The metadata may include data indicating the medical training scenario that the text conversation was based on. The metadata may include a user identifier of the user of the user device 102. The parsing module 116 may tokenize the text of the user message 602. Tokenizing the text may include separating the text into words, phrases, or other text divisions.

Next, in some embodiments, the parsing module 116 may compare one or more tokens of the tokenized user message 602 to the one or more entity data objects 112(1)-(*n*) or activity data objects 114(1)-(*n*). Comparing a token to an entity data object 112 may include comparing the token to the one or more entity values 404 of the entity data object 112. Comparing a token to an activity data object 114 may include comparing the token to the one or more activity values 504 of the activity data object 114. In response to a token matching an entity value 404 or an activity value 504 within a certain threshold, the parsing module 116 may select the entity key 402 or activity key 502 of the corresponding entity data object 112 or activity data object 114. The parsing module 116 may output a computer-readable parsing 604 of the user message 602. The computer-readable parsing 604 may include the one or more entity keys 402 or activity keys 502 that the parsing module 116 selected. The NLP system 110 may send the computer-readable parsing 604 to the server 104.

As an example, as depicted in FIG. 6, the parsing module 116 may receive a user message 602 that includes the text "The patient is experiencing respiratory difficulty." The parsing module 116 may tokenize the user message 602 into multiple tokens: "The," "patient," "is," "experiencing" "respiratory," and "difficulty." The parsing module 116 may compare each token to the entity data objects 112(1)-(*n*) and the activity data objects 114(1)-(*n*) by comparing the token to the entity values 404 or activity values 504 of each entity data object 112 or activity data object 114. For example, an entity data object 112 with the entity key 402 "Patient" may include the entity values 404 "patient," "patients," and "subject." Since the "patient" token matches the entity value 404 "patient," the parsing module 116 may select the "Patient" entity key 402 to include in the computer-readable parsing 604.

Continuing the example, an entity data object 112 with the entity key 402 "Breathing" may include the entity values 404 "breathing," "respiratory," "respiration," and "inhalation." Comparing the "respiratory" token to the "respiratory" entity value 404 may result in the parsing module selecting the "Breathing" entity key 402 to include in the computer-readable parsing 604. After each token has been processed, the parsing module 116 may output the computer-readable parsing 604. The computer-readable parsing 604 may include the selected entity keys 402 and the selected activity keys 502. The computer-readable parsing 604 may arrange the keys 402, 502 in the order the tokens appeared in the user message 602 or in some other order. It should be noted that each key 402, 502 included in the computer-readable parsing 604 shown in FIG. 6 are depicted as enclosed in square brackets to distinguish the keys 402, 502 from text data and to show that keys 402, 502 can include multiple words.

In some embodiments, the parsing module 116 may generate a computer-readable parsing 604 for each user response 602 in a conversation related to a certain medical training scenario. Alternatively, the parsing module 116 may generate a single computer-readable parsing 604 for the medical training scenario by combining multiple user messages 602 that the user submitted during the conversation. In one embodiment, the parsing module 116 may generate a computer-readable parsing 604 corresponding to a phase of the text conversation between the user and the server 104.

In one embodiment, the parsing module 116 may include metadata with the computer-readable parsing 604. The metadata may include the phase corresponding to the user response 602, the medical training scenario corresponding to the user response 602, a user identifier of the user that generated the corresponding user response 602, or other metadata that may be useful in processing or storing the computer-readable parsing 604. The metadata may allow the mapping module 108 to compare the computer-readable parsing 604 to the proper data object that is stored by the server 104, for example, as described below.

Figure 7:
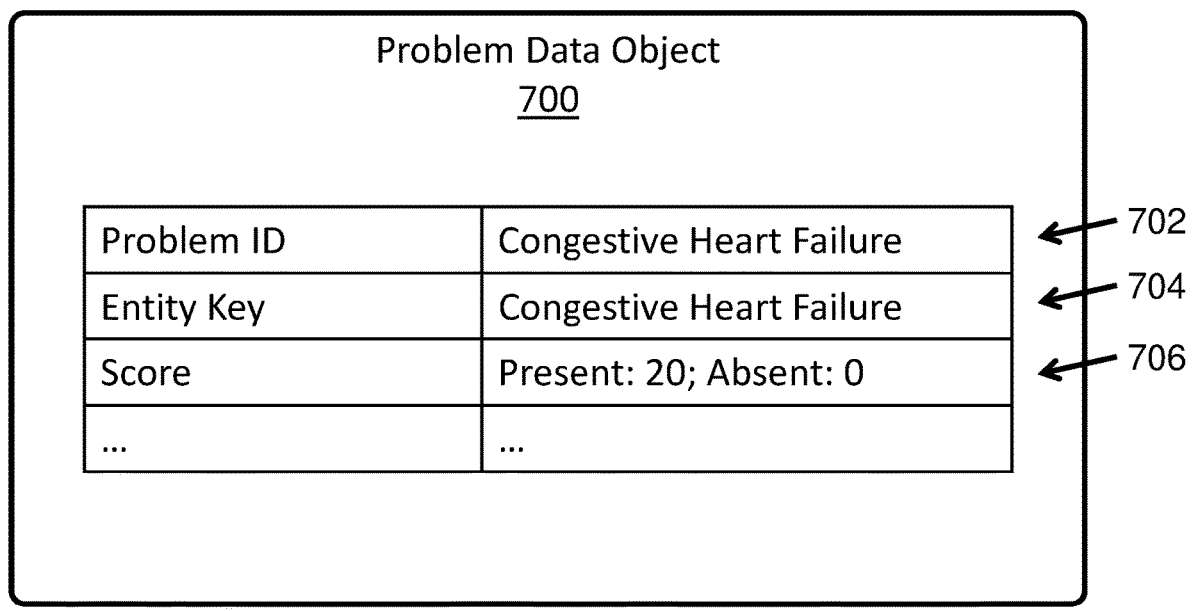
FIG. 7 is a schematic block diagram depicting one embodiment of a problem data object of an artificial intelligence system.

FIG. 7 depicts one embodiment of a problem data object 700. A problem data object 700 may be stored on the server 104. The problem data object 700 may include a problem identification (ID) 702. The problem ID 702 may uniquely identify the problem data object 700 among multiple problem data objects 700. The problem ID 702 may include a brief description of a problem of a medical training scenario. The problem data object 700 may include an entity key 704. The mapping module 108 of the server 104 may compare the entity key 704 of the problem data object 700 to the one or more entity keys 402 of a computer-readable parsing 604 to determine if the computer-readable parsing 604 includes the entity key 704. In one embodiment, the problem data object 700 may include a scoring rubric 706. The scoring rubric 706 may include one or more values that may determine a score for a user in response to a computer-readable parsing 604 including or not including certain entity keys 402 or activity keys 502. A problem data object 700 may include other data.

As an example of a problem data object 700, FIG. 7 depicts a problem data object 700 with a problem ID 702 "Congestive Heart Failure." The entity key 704 includes "Congestive Heart Failure." The scoring rubric 706 includes data such that if the entity key 404 "Congestive Heart Failure" is present in a computer-readable parsing 604, the user receives 20 points, but if the computer-readable parsing 604 does not include the entity key 404 "Congestive Heart Failure," the user receives 0 points.

Figure 8:
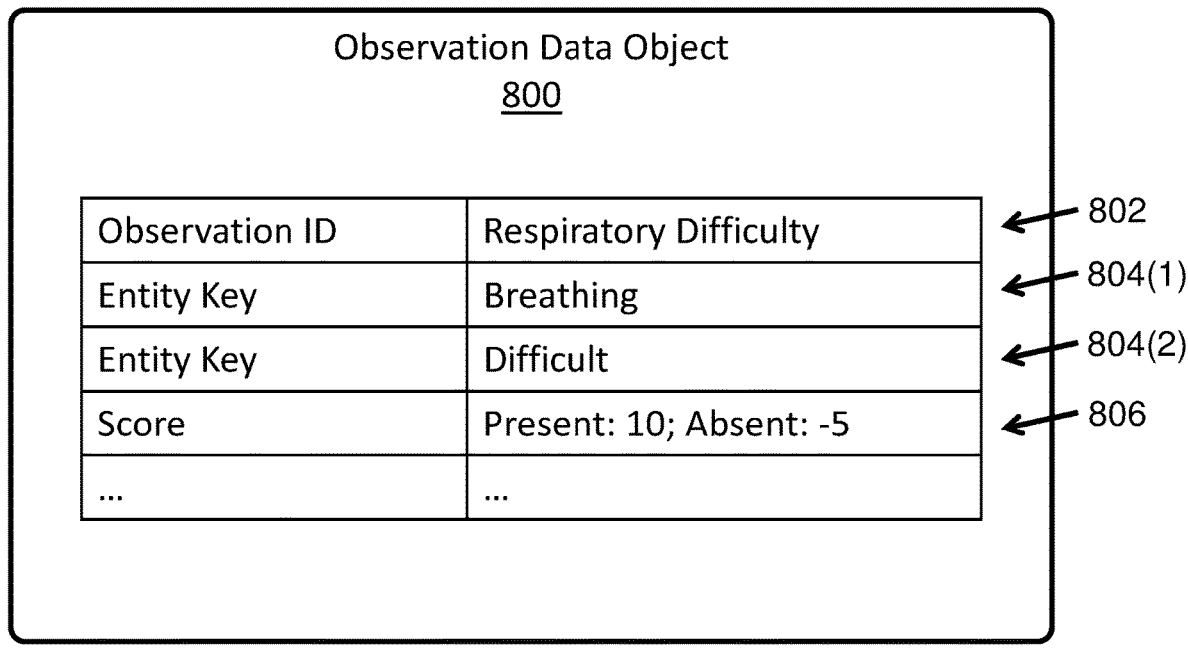
FIG. 8 is a schematic block diagram depicting one embodiment of an observation data object of an artificial intelligence system.

FIG. 8 depicts one embodiment of an observation data object 800. An observation data object 800 may be stored on the server 104. The observation data object 800 may include an observation ID 802. The observation ID 802 may uniquely identify the observation data object 800 among multiple observation data objects 800. The observation ID 802 may include a brief description of an observation that can occur in a medical training scenario. The observation data object 800 may include one or more entity keys 804(1)-(n). The mapping module 108 may compare the one or more entity keys 804(1)-(n) to the one or more entity keys 402 of a computer-readable parsing 604 to determine whether the computer-readable parsing 604 includes one or more of the entity keys 804(1)-(n). The observation data object 800 may include a scoring rubric 806. The scoring rubric 806 may include one or more values that may determine a score for a user in response to a computer-readable parsing 604 including or not including certain entity keys 402 or activity keys 502. An observation data object 800 may include other data.

As an example, the mapping module 108 may process the computer-readable parsing 604 depicted in FIG. 6 based on the observation data object 800 depicted in FIG. 8. In one embodiment, the mapping module 108 may process the computer-readable parsing 604 based on the observation data object 800 because the computer-readable parsing 604 includes metadata indicating that the computer-readable parsing 604 corresponds to the observation phase of a certain medical training scenario. The mapping module 108 may determine that the computer-readable parsing 604 includes the entity key 804(1) "Breathing" and the entity key 804(2) "Difficult." In response, the mapping module 108 may determine that a score for the user is 10. Had the mapping module 108 determined that the computer-readable parsing 604 did not include one or more of the entity keys 804(1) or (2), the score for the user would have been −5.

Figure 9:
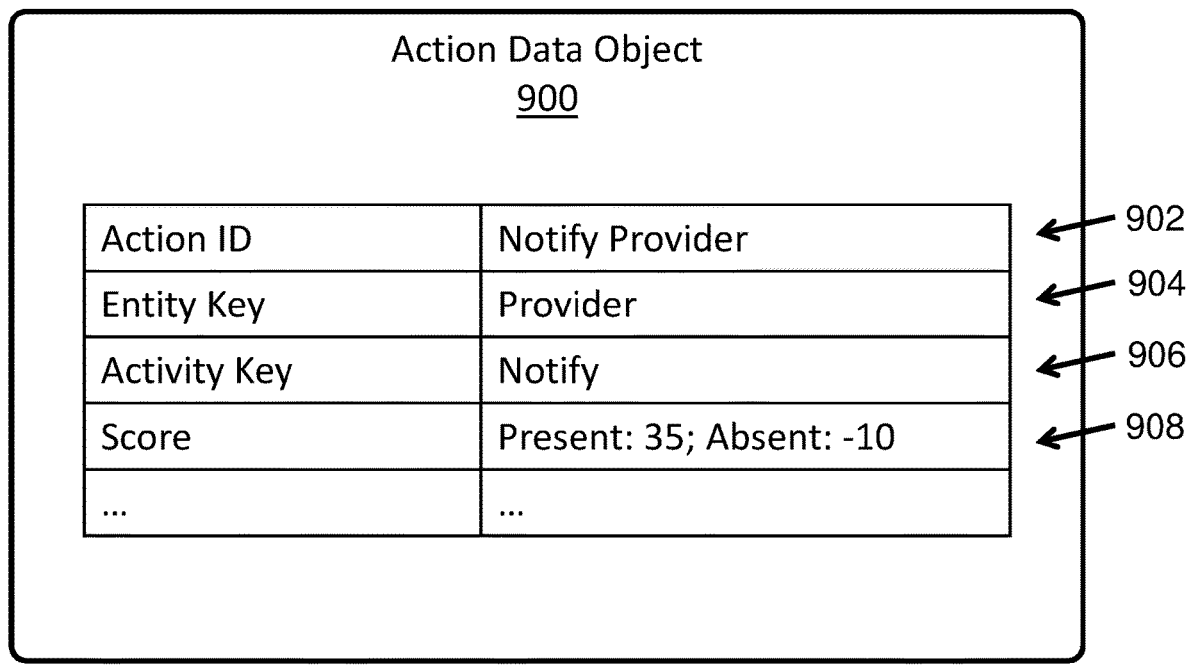
FIG. 9 is a schematic block diagram depicting one embodiment of an action data object of an artificial intelligence system.

FIG. 9 depicts one embodiment of an action data object 900. The action data object 900 may be stored on the server 104. The action data object 900 may include an action ID 902. The action ID 902 may uniquely identify the action data object 900 among multiple action data objects 900. The action ID 902 may include a brief description of an action that can be taken in a medical training scenario. The action data object 900 may include an entity key 904. The action data object 900 may include an activity key 906. The mapping module 108 may compare a computer-readable parsing's 604 entity keys 402 or activity keys 502 to the entity key 904 or activity key 906 of the action data object 900 to determine if the computer-readable parsing 604 includes the entity key 904 or the activity key 906. The action data object 900 may include a scoring rubric 908. The scoring rubric 908 may include one or more values that may determine a score for a user in response to a computer-readable parsing 604 including or not including certain entity keys 402 or activity keys 502. An action data object 900 may include other data.

Figure 10:
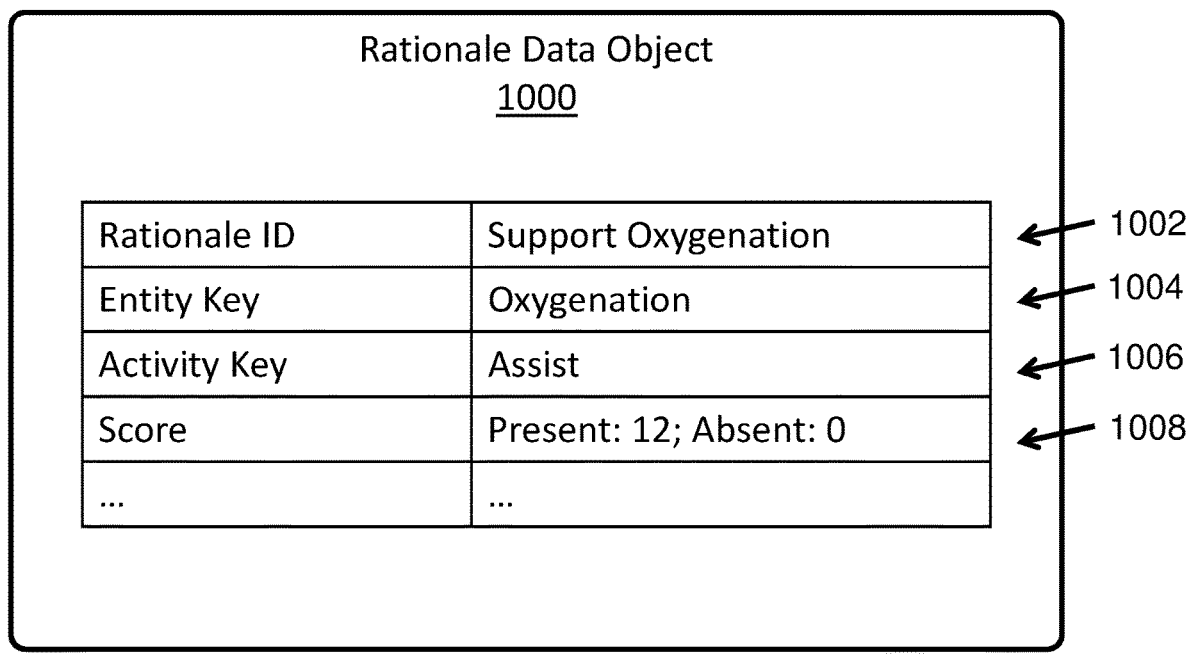
FIG. 10 is a schematic block diagram depicting one embodiment of a rationale data object of an artificial intelligence system.

FIG. 10 depicts one embodiment of a rationale data object 1000. The rationale data object 1000 may be stored on the server 104. The rationale data object 1000 may include a rationale ID 1002. The rationale ID 1002 may uniquely identify the rationale data object 1000 among multiple rationale data objects 1000. The rationale ID 1002 may briefly describe a rationale for observing something or taking a certain action in a medical training scenario. The rationale data object 1000 may include an entity key 1004. The rationale data object 1000 may include an activity key 1006. The mapping module 108 may compare a computer-readable parsing's 604 entity keys 402 or activity keys 502 to the entity key 1004 or activity key 1006 of the rationale data object 1000 to determine if the computer-readable parsing 604 includes the entity key 1004 or the activity key 1006. The observation data object 1000 may include a scoring rubric 1008. The scoring rubric 1008 may include one or more values that may determine a score for a user in response to a computer-readable parsing 604 including or not including certain entity keys 402 or activity keys 502. A rationale data object 1000 may include other data.

In some embodiments, a problem data object 700, observation data object 800, action data object 900, or rationale data object 1000 may include other entity keys 402 or activity keys 502 than those depicted in each data object. For example, even though the observation data object 800 depicted in FIG. 8 has two entity keys 804(1)-(2), in some embodiments, an observation data object 800 may include an entity key 804 and a activity key 502. The observation data object 800 may include two activity keys 502. The observation data object 800 may include some other combination of one or more entity keys 804 and one or more activity keys 502. Similar configurations of entity or activity keys 402, 502 may apply to the other types of data objects 700, 800, 900, 1000.

Figure 11:
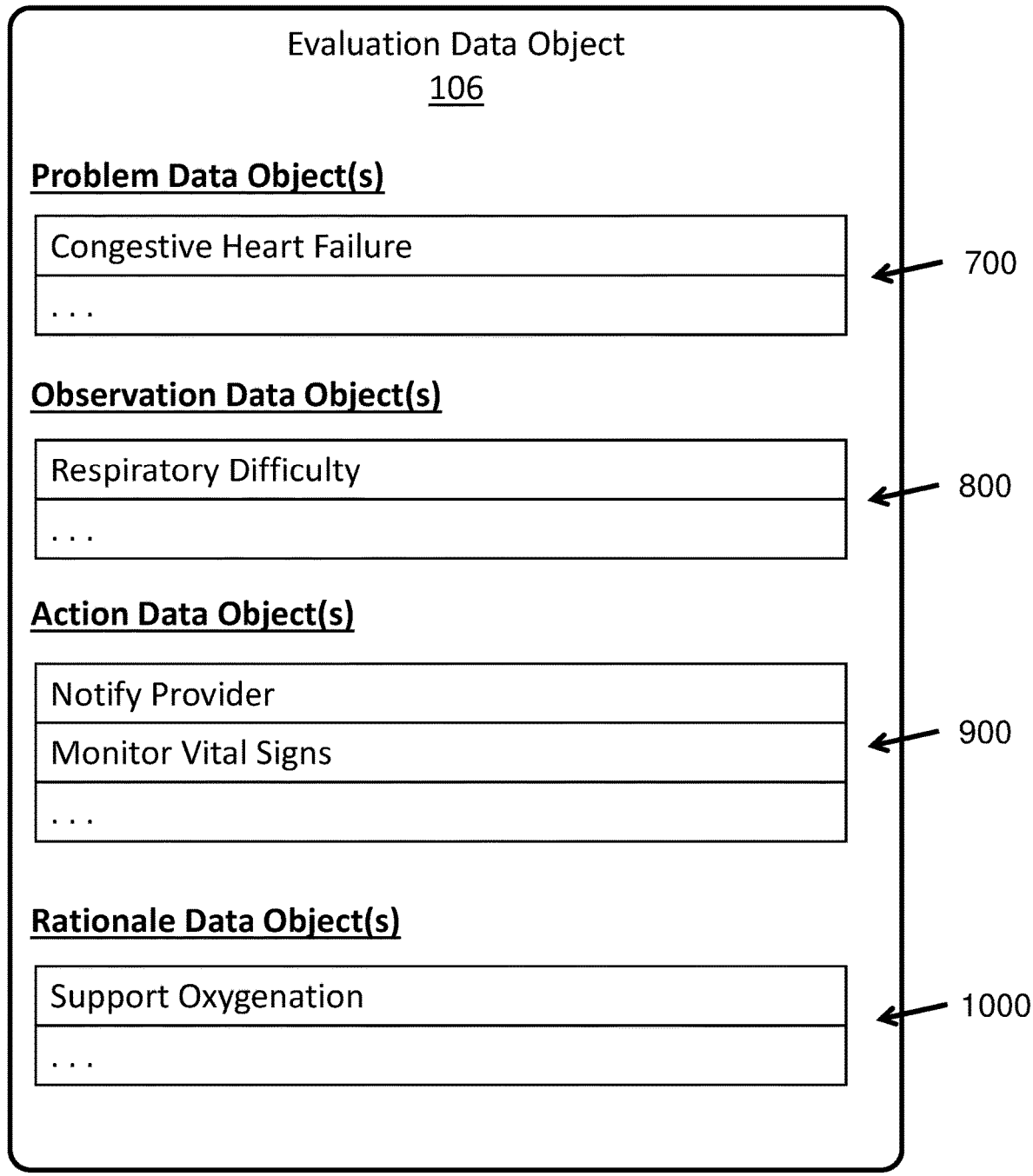
FIG. 11 is a schematic block diagram depicting one embodiment of an evaluation data object of an artificial intelligence system.

FIG. 11 depicts one embodiment of an evaluation data object 106. An evaluation data object 106 may correspond to specified medical scenario information. For example, a first evaluation data object 106(1) may correspond to a congestive heart failure scenario and a second evaluation data object 106(2) may correspond to a bradycardia medical training scenario. In one embodiment, an evaluation data object 106 may include one or more problem data objects 700. The evaluation data object 106 may include one or more observation data objects 800. The evaluation data object 106 may include one or more action data objects 900. The evaluation data object may include one or more rationale data objects 1000.

In some embodiments, the mapping module 108 may compare one or more computer-readable parsings 604 that may have been generated from one or more user responses 602 to the data objects 700, 800, 900, 1000 of the evaluation data object 106 to determine a score for a user. The score may indicate a clinical evaluation judgment for the user that gave the user responses 602.

In one embodiment, the server 104 may compare the user's score to a threshold score. In response to the user's score being below the threshold score, the server 104 may send a link to medical training information to the user device 102. A user interface of the user device 102 may display the link. The user of the user device 102 may select the link to access the medical training information. The medical training information may include a web page, a text document, a portable data file (PDF), or some other information format. The medical training information may correspond to a problem included in the evaluation data object 1100.

As an example, the user of the user device 102 may receive medical scenario information. The problem of the medical scenario information may include bradycardia. The user may enter user responses 602 to questions from the server 104 and the server 104 and the NLP system 110 may process the user responses 602 and determine a score for the user. The user's score may be 75 out of 100. The threshold score may include 85 out of 100. In response to the user's score (75) being lower than the threshold (85), the server 104 may send the user device 102 a link to more information about bradycardia so that the user can improve his or her score.

Figure 12:
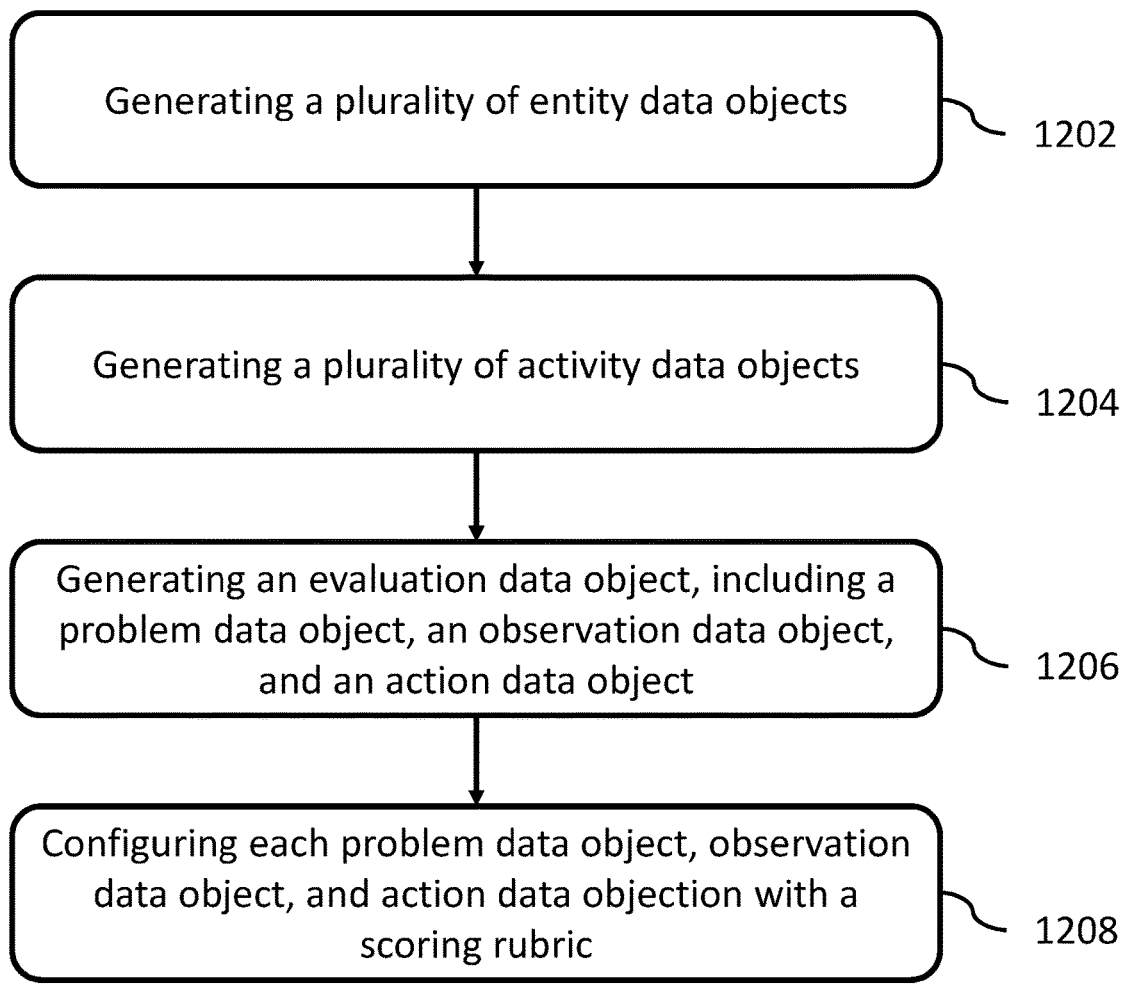
FIG. 12 is a flowchart diagram depicting one embodiment of a method for an artificial intelligence system.

FIG. 12 depicts one embodiment of a method 1200. The method 1200 may include a method for an artificial intelligence system. The method 1200 may include generating 1202 a plurality of entity data objects. Each entity data object may include an entity key 402 and one or more entity values 404 that may correspond to the entity key 402. The step 1202 may occur in an NLP system 110. The method 1200 may include generating 1204 a plurality of activity data objects. An activity data object may include an activity key 502 and one or more activity values 504 that may correspond to the activity key 502. The step 1204 may occur in the NLP system 110.

The method 1200 may include generating 1206 an evaluation data object. The evaluation data object may include a problem data object, an observation data object, and an action data object. The problem data object may include at least one entity key. The observation data object may include at least one entity key. The action data object may include at least one activity key. The method 1200 may include configuring 1208 each problem data object, observation data object, and action data object of the evaluation data object with a scoring rubric.

In one embodiment, generating 1202 the plurality of entity data objects and generating 1204 the plurality of activity data objects may include generating entity data objects 112(1)-(n) or activity data objects 114(1)-(n) as described above. Generating 1206 the evaluation data object may include generating an evaluation data object 106 similar to one described above. Configuring 1208 each problem data object, observation data object, and action data object may include a user configuring such data objects 700, 800, 900 in accordance with data and functionality as described above.

Figure 13:
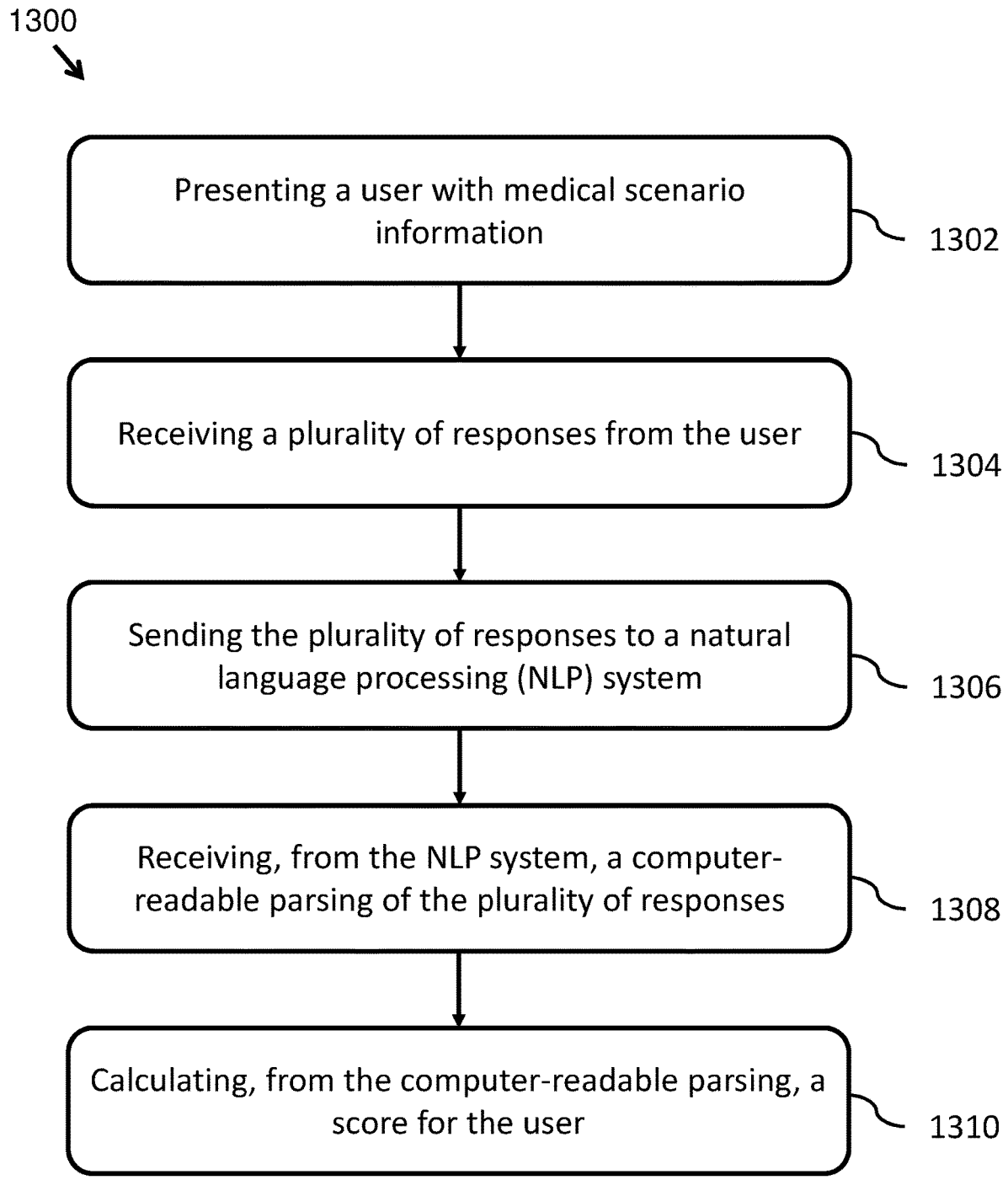
FIG. 13 is a flowchart diagram depicting another embodiment of a method for an artificial intelligence system.

FIG. 13 depicts one embodiment of a method 1300. The method 1300 may include a method for an artificial intelligence system. The method 1300 may include presenting 1302 a user with medical scenario information. The step 1302 may occur via a user interface of a computing device. The method 1300 may include receiving 1304 a plurality of responses from the user. The plurality of responses may include a problem response, an observation response, and an action response. The step 1304 may occur at at least one server.

The method 1300 may include sending 1306 the plurality of responses to an NLP system. The method 1300 may include receiving 1308, from the NLP system, a computer-readable parsing of the plurality of responses. The method 1300 may include calculating 1310, from the computer-readable parsing, a score for the user. The score for the user may indicate a clinical judgement evaluation of the user. The step 1310 may occur at the at least one server.

In one embodiment, presenting 1302 the user with medical scenario information may include presenting the user with the user interface 200 of the FIG. 2. Receiving 1304 the plurality of responses from the user may include receiving, at the server 104, the one or more user messages 350. In some embodiments, receiving 1308 the computer-readable parsing may include receiving a computer-readable parsing 604 that may have been generated by the parsing module 116 of the NLP system 110 based on a user response 602, the entity data objects 112(1)-(n), and the activity data objects 114(1)-(n). Calculating 1310 the score may include the mapping module 108 determining whether the computer-readable parsing 604 includes certain entity keys or activity keys, as described above.

The systems and methods of the present disclosure include improvements to computer functionality. For example, the systems and methods disclosed herein result in automated evaluation of responses from healthcare workers in training. The systems and methods described herein allow computing device to produce accurate and realistic medical training scenario conversations. Furthermore, the systems and methods of the disclosure allow a user in medical training to obtain almost instant feedback regarding a medical training scenario, instead of having to wait for a human to evaluate his or her performance, which happens in conventional approaches.

The systems and method of the present disclosure include unconventional elements and arrangement of elements. These elements and arrangements are not well-understood, routine, or conventional. For example, using a NLP system generate entity data objects and activity data objects that can be used to carry out a medical training conversation and evaluate a user's responses is not a well-understood, routine, or conventional activity. Prompting a user, via a text chat user interface, to identify a problem, observations, actions, and rationales so that they can be submitted in a free response format to a computer for automated grading is also unconventional, and not routine or well-understood.

While the making and using of various embodiments of the present disclosure are discussed in detail herein, it should be appreciated that the present disclosure provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and may be covered by the claims.

Furthermore, the described features, structures, or characteristics of the disclosure may be combined in any suitable manner in one or more embodiments. In the description contained herein, numerous specific details are provided, such as examples of programming, software, user selections, hardware, hardware circuits, hardware chips, or the like, to provide understanding of embodiments of the disclosure. One skilled in the relevant art will recognize, however, that the disclosure may be practiced without one or more of the specific details, or with other methods, components, materials, and so forth. In other instances, well-known structures, materials, or operations may not be shown or described in detail to avoid obscuring aspects of the disclosure.

These features and advantages of the embodiments will become more fully apparent from the description and appended claims, or may be learned by the practice of embodiments as set forth herein. As will be appreciated by one skilled in the art, aspects of the present disclosure may be embodied as an apparatus, system, method, computer program product, or the like. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer-readable medium(s) having program code embodied thereon.

In some embodiments, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer-readable medium(s).

In some embodiments, a module may include a smart contract hosted on a blockchain. The functionality of the smart contract may be executed by a node (or peer) of the blockchain network. One or more inputs to the smart contract may be read or detected from one or more transactions stored on or referenced by the blockchain. The smart contract may output data based on the execution of the smart contract as one or more transactions to the blockchain. A smart contract may implement one or more methods or algorithms described herein.

The computer program product may include a computer-readable storage medium (or media) having computer-readable program instructions thereon for causing a processor to carry out aspects of the present disclosure. The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium may include a portable computer diskette, a hard disk, a random access memory ("RAM"), a read-only memory ("ROM"), an erasable programmable read-only memory ("EPROM" or Flash memory), a static random access memory ("SRAM"), a hard disk drive ("HDD"), a solid state drive, a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present disclosure.

Aspects of the present disclosure are described herein with reference to flowchart illustrations or block diagrams of methods, apparatuses, systems, algorithms, or computer program products according to embodiments of the disclosure. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The schematic flow chart diagrams included herein are generally set forth as logical flow chart diagrams. As such, the depicted order and labeled steps are indicative of one embodiment of the presented method. Other steps and methods may be conceived that may be equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The schematic flowchart diagrams and/or schematic block diagrams in the Figures illustrate the architecture, functionality, and operation of possible implementations of apparatuses, systems, methods and computer program products according to various embodiments of the present disclosure. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Thus, although there have been described particular embodiments of the present invention of new and useful systems and methods for an artificial intelligence system, it is not intended that such references be construed as limitations upon the scope of this invention.

What is claimed is:

1. A computer-implemented method, comprising:
   presenting, via a user interface of a computing device, a user with medical scenario information;
   receiving, at at least one server, a plurality of responses from the user, wherein the plurality of responses include
   a problem response,
   an observation response, and
   an action response,
   sending the plurality of responses to a natural language processing (NLP) system;
   receiving, from the NLP system, at least one computer-readable parsing based on at least a portion of the plurality of responses, wherein
   the at least one computer-readable parsing includes at least one first entity key and at least one first activity key,
   the at least one first entity key includes a text string indicating at least one of a medical condition,
   a medication,
   a medical device,
   a medical supply, or
   a portion of human anatomy, and
   the at least one first activity key includes a text string indicating at least one of
   administering,
   notifying,
   assisting,
   monitoring, or
   experiencing;
   providing an evaluation data object, including
   an observation data object, including at least one second entity key and an observation scoring rubric, and
   an action data object, including at least one second activity key and an action scoring rubric;
   mapping the at least one first entity key to the at least one second entity key of the problem data object by determining whether the at least one first entity key includes the at least one second entity key;

mapping the at least one first activity key to the at least one second activity key by determining whether the at least one first activity key includes the at least one second activity key;

calculating a first sub-score based on the observation scoring rubric and whether the at least one first entity key includes the at least one second entity key;

calculating a second sub-score based on the action scoring rubric and whether the at least one first activity key includes the at least one second activity key; and calculating, by combining the first sub-score and the second sub-score, a score for the user, wherein the score indicates a clinical judgement evaluation of the user.

2. The computer-implemented method of claim 1, wherein presenting the user with the medical scenario information comprises presenting, to the user, at least one of:
   a video;
   one or more vital signs;
   one or more lab values; or
   one or more electrocardiogram (ECG) strips.

3. The computer-implemented method of claim 1, wherein receiving the plurality of responses from the user comprises at least one of:
   receiving a string of text from the user; or
   receiving an audio file from the user.

4. The computer-implemented method of claim 1, wherein the problem response comprises a diagnosis of a medical condition provided by the user and based on the medical scenario information.

5. The computer-implemented method of claim 1, wherein the observation response comprises a observation provided by the user and based on the medical scenario information.

6. The computer-implemented method of claim 4, wherein the action response comprises a user action that responds to the diagnosis of the medical condition.

7. The computer-implemented method of claim 6, wherein:
   the plurality of responses further includes a rationale response; and
   the rationale response includes an explanation of the user action based on the medical scenario information.

8. The computer-implemented method of claim 1, wherein the user interface comprises a text chat user-interface, and wherein the text chat user-interface is configured to receive text data from the user.

9. The computer-implemented method of claim 8, wherein the text chat user-interface is further configured to present to the user a plurality of prompting questions from the at least one server.

10. The computer-implemented method of claim 1, further comprising:
    comparing the score for the user to a threshold score; and
    in response to the score for the user being below a threshold score, presenting to the user, via the user interface, a link to medical training information.

11. The computer-implemented method of claim 10, wherein the medical training information corresponds to a problem identified in the problem response.

12. A computer-readable storage medium, comprising:
    at least one processor; and
    at least one memory storing one or more instructions, wherein the at least one processor, in response to executing the one or more instructions, implements a method comprising
    sending, to a computing device, medical scenario information,
    receiving a plurality of responses from the user, wherein the plurality of responses include
       a problem response,
       an observation response, and
       an action response,
    sending the plurality of responses to a natural language processing (NLP) system,
    receiving, from the NLP system, at least one computer-readable parsing based on at least a portion of the plurality of responses, wherein
       the at least one computer-readable parsing includes at least one first entity key and at least one first activity key,
       the at least one first entity key includes a text string indicating at least one of
          a medical condition,
          a medication,
          a medical device,
          a medical supply, or
          a portion of human anatomy, and
       the at least one first activity key includes a text string indicating at least one of
          administering,
          notifying,
          assisting,
          monitoring, or
          experiencing,
    providing an evaluation data object, including
       an observation data object, including at least one second entity key and an observation scoring rubric, and
       an action data object, including at least one second activity key and an action scoring rubric,
    mapping the at least one first entity key to the at least one second entity key of the problem data object by determining whether the at least one first entity key includes the at least one second entity key,
    mapping the at least one first activity key to the at least one second activity key by determining whether the at least one first activity key includes the at least one second activity key,
    calculating a first sub-score based on the observation scoring rubric and whether the at least one first entity key includes the at least one second entity key,
    calculating a second sub-score based on the action scoring rubric and whether the at least one first activity key includes the at least one second activity key, and
    calculating, by combining the first sub-score and the second sub-score, a score for the user, wherein the score indicates a clinical judgement evaluation of the user.

13. The computer-implemented method of claim 1, wherein:
    the observation scoring rubric comprises a first value and a second value;
    calculating the first sub-score includes
       in response to the at least one first entity key including the at least one second entity key, including the first value of the observation scoring rubric in the first sub-score, and in response to the at least one first entity key not including the at least one second entity key, including the second value of the observation scoring rubric n the first sub-score;

the action scoring rubric comprises a third value and a fourth value; and calculating the second sub-score includes in response to the at least one first activity key including the at least one second activity key, including the third value of the action scoring rubric in the second sub-score, and in response to the at least one first activity key not including the at least one second activity key, including the fourth value of the observation scoring rubric in the second sub-score.

* * * * *